(12) United States Patent
McGlone et al.

(10) Patent No.: US 6,503,492 B2
(45) Date of Patent: Jan. 7, 2003

(54) ANTIPERSPIRANT OR DEODORANT COMPOSITIONS

(75) Inventors: Francis McGlone; Sarah Paterson; Anthony Vincent Rawlings; Roman Rukwied, all of Bebington; Allan Watkinson, Bedford, all of (GB)

(73) Assignee: Unilever Home & Personal Care USA, a division of Conopco, Inc., Chicago, IL (US)

( * ) Notice: Subject to any disclaimer, the term of this patent is extended or adjusted under 35 U.S.C. 154(b) by 0 days.

(21) Appl. No.: 10/079,083

(22) Filed: Feb. 19, 2002

(65) Prior Publication Data

US 2002/0182159 A1 Dec. 5, 2002

(30) Foreign Application Priority Data

Feb. 21, 2001 (GB) ................................ 0104268

(51) Int. Cl.$^7$ ............................ A61K 7/32; A61K 7/34; A61K 7/38; A61K 7/08
(52) U.S. Cl. ............................ 424/65; 424/65; 424/66; 424/68; 424/400; 424/401
(58) Field of Search ............................ 424/65, 66, 68, 424/400, 401

(56) References Cited

U.S. PATENT DOCUMENTS

| | | | | |
|---|---|---|---|---|
| 4,781,917 A | * | 11/1988 | Luebbe et al. ................ 424/65 |
| 5,407,668 A | | 4/1995 | Kellner ........................ 424/65 |
| 5,679,667 A | * | 10/1997 | Della Valle et al. ........ 514/182 |
| 5,990,170 A | * | 11/1999 | Della Valle et al. ........ 514/613 |

FOREIGN PATENT DOCUMENTS

EP 550 006 9/1999

OTHER PUBLICATIONS

GB Search Report in a GB application GB 0104268.8.

* cited by examiner

*Primary Examiner*—Shelley A. Dodson
(74) *Attorney, Agent, or Firm*—Kevin J. Stein

(57) ABSTRACT

Deodorant and antiperspirant compositions comprising an aluminium or aluminium-zirconium active can suffer from perceived irritancy when applied topically, which is generally manifested as an itch sensation. This irritancy can be ameliorated or overcome by incorporating within the composition a cannabanoid receptor (CBR) activating agent, and especially an amount selected in the range of from 0.25 to 10 wt %.

14 Claims, No Drawings

ANTIPERSPIRANT OR DEODORANT COMPOSITIONS

The invention relates to antiperspirant or deodorant compositions intended for topical application to human skin. In particular, it relates to antiperspirant or deodorant compositions comprising an agent that is capable of ameliorating or controlling skin irritancy.

BACKGROUND

In many countries, civilised behaviour encourages people to take steps to prevent or control body odours or visible wet patches caused by sweating, particularly in the underarm or on clothing in the vicinity of the underarm. People in some countries prefer to control both sweat and odour, whereas in other countries control of odour alone is favoured.

The antiperspirant market is currently dominated by topically applied products based on aluminium or zirconium salts which are intended to prevent, or at least control, localised perspiration at the skin surface, particularly on the underarm. Such formulations can often simultaneously provide a perceived degree of deodorancy.

In contrast, deodorants are formulations that are designed either to mask malodour or to prevent or hinder its formation. The latter method usually comprises reducing and/or controlling the re-growth of the local micro-organism populations, or targeting preferentially those bacteria such as a sub-class of Coryne bacteria which contribute disproportionately to axillary odour generation, or interrupting the pathways by which malodours are formed from secretions.

Antiperspirant and deodorant formulations are utilised in many applicator forms e.g. roll-ons, creams or soft solids, gels, firm sticks, aerosols and pump sprays. However all forms can suffer from a number of common disadvantages.

A principal disadvantage of many deodorants and antiperspirants is that they contain one or more commonly employed ingredients which are perceptibly unfriendly to human skin in those areas of the body to which the formulations are normally applied. Such ingredients are usually employed because they demonstrate other attributes which are advantageous or otherwise render the formulation particularly effective. Such essential or otherwise highly desirable ingredients include liquid carriers such as volatile silicones and ethanol, and indeed many deodorant or antiperspirant actives as well as a host of other ingredients commonly employed in deodorant and antiperspirant formulations. Such ingredients are perceived to exhibit an adverse effect, in particular an irritant effect, on a user's skin following application. Of those ingredients, particular attention may be accorded to aluminium and zirconium salts and complexes that act as antiperspirants.

Physiologically, irritation in the underarm usually adopts either or both of two forms, which are not mutually exclusive. It can manifest itself as redness due to inflammation or as noxious somatosensory responses such as pruritus (itch), sting and/or burn.

Skin unfriendliness can be tolerated, at least to some extent, which will vary from user to user, but it would be advantageous to identify means of reducing or eliminating the effect. Manifestly, irritation can be ameliorated by lowering the amount of any offending active ingredient in the formulation, but a serious drawback of such an approach is that the efficacy of the ingredient would be impaired.

Rather than look only empirically for materials which can demonstrate skin benefits in an antiperspirant or deodorant formulation, the inventors of the present invention have investigated mechanisms within skin cells which generate irritancy and related adverse skin conditions in humans and have sought means to alleviate or control those mechanisms.

Mankind has sought therapeutic means to relieve pain and suffering ever since records have been kept. Early remedies involved the administration of natural products, commonly by ingestion, topical application or inhalation, presumably as a result of empirical observations. For example, *Cannabis sativa*, colloquially called cannabis, or extracts therefrom, has been employed therapeutically for approximately 3000 years, being first mentioned in the time of Emperor Shen Nung in the *Chinese Compendium of Medicine*. It has subsequently been suggested that its perceived efficacy can be due to the action of $\Delta^9$-tetrahydrocannabinol. Cannabinoid agents have been asserted to have anti-inflammatory actions (A. W. Wirth et al., Life Sci. 26, 1991–1995 (1980)). More recent research has shown that the biological actions of cannabis are mediated by two similar, but distinct, types of membrane receptor which have been termed Cannabinoid Receptor 1 (CB1R) and Cannabinoid Receptor 2 (CB2R) (Matsuda et al, Nature 346, 561–564 (1990), Munro et al, Nature, 365, 61–65 (1993)).

CB1R is by far the predominant form in the central nervous system, whereas both CB1R and CB2R are located in the peripheral tissues, including the skin. Some investigations have been made to locate natural endogenous ligands that can activate one or other of these receptors. Herein a reference to a CBR activator includes either or both CB1R and CB2R activators.

Arachidonylethanolamide (anandamide) has been stated to exhibit a greater affinity for the CB1R compared with CB2R and is believed to be the endogenous CB1R agonist (Pertwee et al, Br. J. Pharmacol. 105, 980–984 (1992)). It has been suggested that palmitoylethanolamide and 2-arachidonyl-glycerol are putative CB2R agonists (Facci et al, Proc. Natl. Acad. Sci. 92, 3376–3380 (1995), Sugiura et al., J. Biol. Chem. 275, 605–612 (2000)). Ligands that activate both CB1R and CB2R have been shown to be analgesic, whether applied systemically or cutaneously (Calignano et al, Nature,394, 277–280 (1998)).

Therapeutic uses have already been contemplated involving CBRs. For example, U.S. Pat. No. 5,990,170 (Della Valle et al) teaches the therapeutic use of a range of selected mono and dicarboxylic acid amides which bind the CB2R in order to treat diseases connected with this receptor. EP-A-550006 (Della Valle et al) teaches that a range of N-acyl derivatives of amino alcohols to be used for the treatment of pathologies characterised by the degranulation of mast cells. U.S. Pat. No. 5,679,667 describes the use of amino alcohols-N-acyl derivatives as therapeutic agents against neurogenic endoneural edema of the peripheral nerve. However, none of these references disclose or contemplate in any way antiperspirant or deodorant formulations or the use of any of the actives disclosed therein in such formulations.

During the last century, many different classes of compounds have been proposed in patent or other publications for incorporation in antiperspirant or deodorant formulations. However, none of such antiperspirant or deodorant publications have disclosed the subject of the present invention, either knowingly or unwittingly, for example because the compounds that are disclosed in them for other purposes are inactive for the present purpose, even though some of them may be chemically related to an active compound. Alternatively, the selection of ingredients of the instant invention has not been disclosed.

Thus, for example, U.S. Pat. No. 4,781,917 (Luebbe et al) describes the use of different monoethanolamides such as coconut mono- or stearamide monoethanolamide in antiperspirant gel sticks that do not exhibit the advantageous properties required for the instant invention. In addition, U.S. Pat. No. 5,407,668 (Kellner) teaches of the use of a class of alkanolamides in clear deodorant stick compositions as a component of a clarity enhancing solubilizer system, but does not contemplate expressly the presence of aluminium or zirconium antiperspirant salts or complexes. Accordingly, '668 does not teach how to select materials to satisfy the instant invention.

SUMMARY OF THE INVENTION

According to the invention there is provided an antiperspirant or deodorant cosmetic composition suitable for topical application to the human skin, characterised by comprising:
  i. an antiperspirant or deodorant active comprising an aluminium and/or zirconium salt or complex;
  ii. a carrier for the antiperspirant or deodorant active; and
  iii. an effective amount of a CBR activating agent.

By the employment of a CBR activating agent in an effective amount in an antiperspirant or deodorant formulation containing an aluminium and/or zirconium salt or complex, it is possible for users of such formulations to experience reduced or no irritancy such as itch or like skin complaints on areas of the skin to which formulation has been applied.

The capability of a compound to act as a CBR activating agent can be determined using a topical application test on human skin in which the irritant effect of a predetermined concentration of a known irritant, for example a known pruritic agent, such as histamine, is counteracted by chosen amounts of the target compound.

DETAILED DESCRIPTION OF THE INVENTION AND PREFERRED EMBODIMENTS

The present invention relates to the incorporation of a CBR activating agent in antiperspirant or deodorant compositions. The effectiveness of a material to act as a CBR activating agent can be determined by incorporating it in an antiperspirant or deodorant composition and observing the extent to which redness, itch, sting or burn is diminished.

It can be convenient to employ a topical application test as a way of demonstrating whether the test material would be effective as a CBR activating agent. In one such test employing the control conditions described subsequently herein, human skin is contacted with a control or test material under a water-impermeable patch for a specified length of time, such as 24 hours and then challenged with a predetermined dose of a known irritant such as histamine applied by iontophoresis at a specified current for a specified period, e.g. 10 seconds at 50 $\mu$A, which is counteracted by application of a test material within a range of concentrations so as to be able to identify that at which the material becomes effective. By plotting the perceived strength of the response against time, a test value can be obtained which comprises the area under the curve. This area is normally that from time 0 to 5 minutes and the base line at 0 to the response curve. In an alternative, but related, test procedure, a cream formulation is applied topically to the skin, for example for a period of 4 hours rather than being covered by a patch, and is then challenged in the same way.

The measured activity of test material can vary between subjects. Accordingly, an averaged result should be employed. The test material can be considered to pass the histamine test at its chosen concentration when the averaged test value from histamine plus the test material is less than 80% of the control test value, i.e. that obtained from histamine without the test material under the same test conditions. Preferably, the material and its amount are chosen in combination such that the resultant averaged test value is not higher than 50% of the control test value.

In such a test, the difference necessary for it to be statistically significant decreases as the number of subjects in the test increases. For the most effective CBR activating agents, a small number of subjects can demonstrate a positive result, whereas for less active agents, it is desirable to employ a larger number such as at least 20 subjects and preferably about 50.

Herein a material is considered to be a CBR activating agent, if it passes the foregoing test or any other test method for CBRs described herein.

It is particularly desirable to identify and employ a compound that can act as an activating agent for a CBR ie for either or both CB2R and CB1R, on account of the presence of both CB1R and CB2R sites in skin.

Examples of CBR activating agents (iii) include:
2-arachidonyl-glycerol
1-arachidonyl-glycerol
3-arachidonyl-glycerol
2-linoleoyl-glycerol
2-linolenoyl-glycerol
2-eicosatrienoyl-glycerol
2-eicosatetraenoyl-glycerol
2-eicosapentenoyl-glycerol
2-eicosahexaenoyl-glycerol
Palmitoylethanolamide
(6aR)-trans-3-(1,1-Dimethylheptyl)-6a,7,10,10a-tetrahydro-1-hydroxy-6,6-dimethyl-6H-dibenzo[b,d]pyran-9-methanol, sometimes called HU-210 herein;
Indomethacin morpholinylamide sometimes abbreviated to IMMA herein;
mesylate: (R)-(+)-[2,3-Dihydro-5-methyl-3-(4-morpholinylmethyl)pyrrolo[1,2,3-de]-1,4-benzoxazin-6-yl]-1-naphthalenylmethanone, sometimes called WIN55212-2 herein; (−)-cis-3-[2-Hydroxy-4-(1,1-dimethylheptyl)phenyl]-trans-4-(3-hydroxypropyl)cyclohexanol, sometimes called CP55940 herein;
R-(+)-Methanandamide: [R-(all-Z)]-N-(2-Hydroxy-1-methylethyl)-5,8,11,14-eicosatetraenamide;
Arachidonyl-2'-chloroethylamide: (all Z)-N-(2-cycloethyl)-5,8,11,14-eicosatetraenamide);
Arachidonylcyclopropylamide: (all Z)-N-(cyclopropyl)-5,8,11,14-eicosatetraenamide;

It will understood that, for example, although palmitoyl ethanolamide acts as a CBR activating agent, ethanolamides which are structurally similar, but derived from related aliphatic acids such as stearic acid or linoleic acid do not act as CBR activating agents, even though for various other purposes they would be classified within the same generic class.

Naturally occurring precursors of said CBR activating agents can also be employed herein, generating the activating agent for example by hydrolysis on the skin.

Mixtures of two or more of said can be employed herein, such as a combination of palmitoylethanolamide with an aforementioned glycerol derivative, for example in a weight ratio of from 10:1 to 1:10.

The amount of CBR activating agent (iii) in the invention compositions is preferably selected in the range of from at least 0.05%, and often to not more than 20%, more preferably in some embodiments from 0.1% and in those or other embodiments up to 10%, as herein being by weight based on the formulation or base formulation, as the case may be, unless otherwise stated. In a number of practical formulations, the concentration of CBR activating agent is not more than 5%, and particularly from 0.25 to 2 wt %.

An antiperspirant composition according to the invention comprises an antiperspirant active comprising an aluminium and/or zirconium salt or complex (i). The proportion of antiperspirant active present in the composition according to the invention may be from 1–35% by weight of the composition, preferably at least 5% by weight and more preferably 15–30% by weight of the base composition. A base composition herein excludes any propellant which may be employed.

Examples of suitable actives (i) include aluminium salts, zirconium salts, aluminium and/or zirconium complexes, for example aluminium halides, aluminium hydroxy halides, zirconyl oxyhalides, zirconyl hydroxyhalides, and mixtures thereof. Specific examples include activated aluminium chlorohydrate, aluminium chlorohydrate, aluminium pentachlorohydrate and aluminium zirconium chlorohydrate. Useful zirconium salts include zirconium hydroxy-chloride and zirconium oxychloride. Other generally used actives will be known to those skilled in the art. Preferred actives include ZAG (Zirconium Aluminium Glycine), AAZG (Activated Aluminium Zirconium Glycine), and AACH (Activated Aluminium Chorohydrate). The antiperspirant active can be present in particulate form whereupon it is normally suspended in a suitable carrier fluid, which usually is water-immiscible, and which can be structured or thickened. Alternatively the active can be dissolved in a polar solution, such as for example in aqueous solution or in a polar low weight polyhydric alcohol such as propylene glycol, advantageously 30 to 60% by weight solution.

It is a benefit of the present invention that incorporation of a CBR activating agent in an effective amount can improve the acceptability of conventional antiperspirant-containing formulations, such as those containing an astringent antiperspirant active, by reducing the risk of irritancy.

The deodorant compositions according to the present invention normally comprise 0.01 to 90% of a deodorant active. Deodorancy can be provided by the aforementioned aluminium and/or zirconium antiperspirant salts or complexes, optionally with an additional deodorant active, such as any deodorant active known in the art such as alcohols, in particular aliphatic monohydric alcohols such as ethanol or propanol, antimicrobial actives such as polyhexamethylene biguanides eg those available under the trade name Cosmocil™ or chlorinated aromatics, eg triclosan available under the trade name Irgasan™, non-microbiocidal deodorant actives such as triethylcitrate, bactericides and bacteriostatis. Yet other deodorant actives can include zinc salts such as zinc ricinoleate.

The antiperspirant active salt or complex (i) and the CBR activating agent (iii) can conveniently be employed in a weight ratio of from 1:1 to 100:1, often at least 5:1, and in many instances up to 50:1.

The carrier material for the compositions according to the invention can comprise one or more of volatile carrier fluids, one or more of non-volatile emollients, and it can be structured or thickened by one or a combination of thickener and/or structurant materials if required. The carrier material, including, where relevant, carrier materials providing additional properties such as emolliency, can often comprise up to about 99 wt %, in many instances from 5 to 90 wt % and particularly from 10 to 70 wt % of the composition, or of the base composition, if mixed subsequently with a propellant. Where the composition comprises both hydrophilic and hydrophobic phases, the weight ratio of the two phases is often in the range of 10:1 to 1:10. Aerosol compositions according to the present invention can conveniently be obtained by introducing a base formulation as described herein that is free from propellant and at least 0.7 times and often 1.5 to 20 times its weight of propellant into a suitable aerosol dispenser.

The antiperspirant or deodorant composition can comprise a mixture of particulate solids or a suspension of solids in a liquid medium, which can be thickened to reduce the rate of segregation or structured to produce a cream (soft solid) or solid. Alternatively the composition can comprise a mixture of liquid constituents, including a solution of an active in a carrier, such a composition often adopting the form of an oil-in-water or water-in-oil emulsion, which may be thickened or gelled.

The carrier material, which may be a fluid or a mixture of fluids, is often selected according to the physical form of the cosmetic composition, e.g. volatile low viscosity silicones, low molecular weight hydrocarbons, alcohols and water, and can be selected by those skilled in the art to provide appropriate physical and sensory properties for the product. It will be understood that certain fluid alcohols such as in particular ethanol can constitute both a carrier and a deodorant active simultaneously, though advantageously formulations containing such a material also contain an additional deodorant and/or antiperspirant active.

Volatile silicones are usually selected from cyclic polysiloxanes containing from 3 to 8 dialkylsilicone groups, especially dimethylsilicone groups and particularly 4 or 5 dimethylsilicone groups. Other useful volatile silicones can comprise linear polysiloxanes, preferably containing 4 or 5 alkylsiloxane groups, including terminal groups. Low molecular weight liquid hydrocarbons can comprise paraffin oils. Suitable alcohols can comprise monohydric alcohols, such as C3 to C10 aliphatic alcohols, dihydric alcohols such as glycol or propylene glycol or polyhydric alcohols such as glycerol or sorbitol. Carrier materials can provide additional desirable properties, such as polyhydric alcohols for example glycerol can act as a moisturising agent and volatile cyclomethicones can act as emollients.

The non-volatile emollient, if used in the composition, may consist of a single emollient compound or a mixture of emollients. Such emollients often have a solubility parameter of below 10 and many of from 5.5 to 9. They can typically include saturated fatty acids and fatty alcohol esters, ethers containing aliphatic and a polyalkylene group, hydrocarbons, water insoluble ethers, mineral oils and polyorganosiloxanes, and mixtures thereof.

Non-volatile silicones are often polyalkylsiloxanes, polalkylarylsiloxanes or polyethersiloxanes having a viscosity of above 10 mPa.s, such as up to about $5\times10^6$ mPa.s at 25° C., including polymethylphenylsiloxanes or dimethylpolyoxyalkylene ether copolymers.

Emollient aliphatic esters, often containing from about 12 to 25 carbons, and preferably one substituent containing a chain of at least 12 carbons. Examples include cetyl palmitate, butyl myristate, glyceryl stearate and propylene glycol monolaurate. The composition cam comprise a liquid aliphatic ether which can provide emolliency, such as ethers derived from polyalkyene glycols and a low weight (eg up to C6) alcohol, such as polypropylene glycol (10–15) butyl ether.

The total amount of emollient materials within the composition is often within the range of from 1 to 70 wt %.

The thickening or structurant agent, when required, is selected according to the product form of the cosmetic composition. The thickening or structuring agent can be organic (monomeric or polymeric) or inorganic and is usually chosen depending on the physical nature of the liquid phase to be thickened or structured, such as whether it is hydrophobic or hydrophilic. The amount is normally selected in order to attain the desired viscosity of the liquid or cream or desired resistance to penetration of a solid containing the PPAR fatty acid or precursor thereof in accordance with the present invention.

The thickener or structurant can be any of a number of materials, including, for example, waxy structurants for a formulation containing a water-immiscible phase including hydrogenated vegetable oil, hydrogenated castor oil, fatty acids, such as 12-hydroxystearic acid (12-HSA), or ester or amide derivatives of such acids, beeswax, paraffin wax, microcrystalline waxes, silicone wax, and fatty alcohols, such as stearyl alcohol. The structurant can also be a fibre-forming gellant, of which 12-HSA is an example. Other examples include N-acyl amino acid amides and esters, including particularly GP-1 (N-Lauroyl-L-glutamic acid di-n-butylamide), lanosterol, combinations of a sterol and a sterol ester, such as especially β-sitosterol and χ-oryzanol, a polyesterified cellobiose, especially with a C8 to C10 aliphatic acid, threitol esters or and selected secondary amides of di or tri basic carboxylic acids, (eg 2-dodecyl-N,N'-dibutylsuccinimide) by themselves or in combination.

Polymeric materials for thickening include polymers such as polyamides, hydroxypropylcellulose, and natural or synthetic gums, such as polyglycerides including agar, agarose, pectin, or guars or mixtures or combinations thereof. One class of materials worthy of attention for thickening a water-immiscible phase comprises derivatives of hydrolysed starch or other polysaccharides, including in particular esterified dextrins, such as dextrin palmitate. A further class of polymers that is particularly directed to structuring an oil phase containing a silicone oil comprises polysiloxane elastomers. Suspending agents such as silicas or clays such as bentonite, montmorillonite or hectorite, including those available under the trademark Bentone can also be employed to thicken liquid compositions according to the invention. The composition can be thickened with non-polymeric organic gellants, including selected dibenzylidene alditols (eg dibenzylidene sorbitol).

The amount of structurant or thickening agent that can be employed in the invention compositions will depend upon the viscosity of a fluid formulation or extend of hardness of a solid formulation that the producer wishes to attain. The amount to be employed will in practice also vary depending on the chemical nature of the structurant or thickening agent. In many instances, the amount of structurant or thickening agent will be selected in the range of from 0.1 to 25 wt %, and particularly from 1 to 15 wt %.

The composition according to the invention can optionally comprise other ingredients, in addition to those already identified, depending on the nature and form of the finished product.

Other ingredients contemplated within the personal deodorant or antiperspirants art can also be included in the compositions according to the invention. These include, for example, surfactants/wash-off agents, fillers, fragrances, antioxidants, preservatives and colouring agents. Such ingredients and their amounts of use are usually selected according to the physical and chemical form of the cosmetic composition.

Surfactants can comprise optionally up to 15%, more commonly up to 5% by weight of the total product, and are particularly useful in formulating emulsion antiperspirant or deodorant compositions, for example for use as pump spray or roll-on formulations. However for other product types, it is preferred that the composition contains less than about 8% by weight of surfactants. Non-ionic surfactants are particularly preferred. It is often convenient to select a mixture of surfactants, such as one having a comparatively high HLB value, eg 8 to 18, and one having a comparatively low HLB value, eg 2 to 8, which can be introduced in suitable relative proportions to to attain an average HLB value of about 6 to 12.

Many suitable nonionic surfactants are selected from nonionic esters, ethers or amine oxides having an appropriate HLB value. Many preferred ionic surfactants comprise a polyoxyalkylene moiety, especially a polyoxyethylene moiety eg 2 to 80, especially 5 to 60 oxyethylene units, or possibly with a polyoxypropylene content, to provide hydrophilicity. Other moieties providing hydrophilicity include polyhydric alcohols such as sorbitol or glycerol. The hydrophobic moiety is commonly derived from aliphatic alcohols or acids or amines containing about 8 to 50 carbons and particularly 10 to 30 carbons. Examples of suitable nonionic surfactants include ceteareth-10 to -25, ceteth-10 to -25, steareth-10 to -25, and PEG-15 to -25 stearate or PEG-8 distearate. Other suitable examples include C10–C20 fatty acid mono, di or tri-glycerides. Further examples include C18–C22 fatty alcohol ethers of polyethylene oxides (8 to 12 EO).

Examples of surfactants which typically have a low HLB value, often from 2 to 8, can comprise mono or possibly di fatty acid esters of polyhydric alcohols such as glycerol, sorbitol, erythritol or trimethylolpropane, including cetyl, stearyl arachidyl and behenyl derivatives.

Fillers can comprise up to about 20%, more commonly up to 10% of the base composition and can act as supports for liquid ingredients. Suitable fillers include aluminium stearate, aluminium tri-stearate, calcium stearate, talc or finely divided polyethylene, an example of which is ACUMIST B18. The latter can also enhance skin feel properties.

Fragrances, when present, typically comprise up to about 4% of the total product and often from 0.1 to 1.5%.

Colouring agents antioxidants such as ascorbic acid and tocopherol and preservatives such as C1 to C3 alkyl parabens can be added as desired.

Other optional ingredients are other cosmetic adjuncts conventionally employed or contemplated for employment in antiperspirant or deodorant products.

The ingredients which can optionally be present in the composition carrier can conveniently form the balance of the composition.

Propellants commonly employable in aerosol compositions herein commonly comprise hydrocarbons or halohydrocarbons such as fluorohydrocarbons, having a boiling point of below 10° C. and especially those with a boiling point below 0° C. It is especially preferred to employ liquified hydrocarbon gases, and especially $C_3$ to $C_6$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane. Other or additional propellants include fluorinated low molecular weight hydrocarbons. Yet still other propellants can include volatile ethers or carbon dioxide.

The relative weight proportions of propellant and base composition is often selected at least 40:60 and particularly at least 60:40. The proportions in many embodiments are up to 99:1 and particularly up to 95:1. Commonly, proportions are selected in the range of at least 70:30 and in the same or other formulations the proportions are up to 90:10.

Compositions according to the invention can be provided in any form of a product suited to or adapted for topical application to human skin, and is usually contained in a suitable holder or dispenser to enable it to be applied to the selected area of the skin, particularly the underarm, where control of perspiration and/or deodorancy is desired.

Having described the invention in general terms, specific embodiments thereof will now be described in greater detail by way of example only.

EXAMPLE 1

Effect of topically applied HU-210 on histamine-induced itch.

In this demonstration, a material was tested to see if it was a CBR activating agent. HU210 was dissolved in Aqueous Cream BP at a concentration of 0.5% and 0.05% (w/v) and topically applied to the volar forearm skin: five applications of 50 µl per 3 cm$^2$ area, and itching perception was determined after 4 hours. The control site contained the vehicle alone and the study was performed in a double-blind fashion. The cream covered area was then treated with histamine applied by iontophoresis to induce itch. In summary, a 1% histamine solution in 1% methylcellulose was placed in the iontophoretic chamber and a 10 sec burst of 50 µA was applied using an Iontophoresis Controller MIC-e (Moors Instruments, of Axminster, U.K.). After application of the current, each subject indicated the intensity of the itch sensation, by moving a slider to the appropriate point on a Visual Analogue Scale (VAS), which ranges from threshold sensation (0) to maximal itch (10), to indicate the subject's itch response. VAS readings were taken for 5 minutes following histamine application and plotted against the time of the reading. The VAS value shown in subsequent tables of results comprises the area under the curve from 0 to 5 minutes. The results are summarised in Table 1 below. The formulation of the Aqueous Cream B.P. comprised:

cetylstearyl alcohol 8.1% w/w sodium lauryl sulphate 0.9% w/w liquid paraffin 6.0% white soft paraffin 15.0% w/w water—balance.

TABLE 1

| Treatment | | | Itch score | |
|---|---|---|---|---|
| | Vehicle | HU-210 amount | Itch score (area under the curve) | % of control |
| Control | yes | 0 | 1634 | 100 |
| 1.1 | yes | 0.05% | 101 | 7.3 |
| 1.2 | yes | 0.5% | 119 | 6.2 |

The results in Table 1 show that HU-210 is capable of reducing histamine-induced itch when topically applied and is indicative of the capability of CBR activating agents to alleviate itch.

EXAMPLE 2

Effect of Palmitoylethanolamide applied by patch on histamine-induced itch.

In this demonstration of whether a test material was a CBR activating agent, the method of Example 1 was followed except for employing palmitoylethanolamine (PEA, 100 mM) in 50% ethylene glycol: 50% ethanol instead of HU-210 (in an aqueous Cream BP) at the specified concentration, and applied to the skin under a water-impermeable patch for 24 hours before the histamine challenge. The method was carried out four times. The results are summarised in Table 2 below.

TABLE 2

| | Treatment | Itch score (area under curve) | Itch score % of control |
|---|---|---|---|
| Control | Vehicle alone | 500 | 100 |
| 2.1 | Vehicle + PEA | 129 | 26 |
| Control | Vehicle alone | 377 | 100 |
| 2.2 | Vehicle + PEA | 103 | 27 |
| Control | Vehicle alone | 701 | 100 |
| 2.3 | Vehicle + PEA | 545 | 78 |
| Control | Vehicle alone | 56 | 100 |
| 2.4 | Vehicle + PEA | 32 | 57 |

From Table 2, it can be seen that the CBR activating ligand PEA can inhibit histamine-induced itch. The population exhibits a wide variation in response to histamine-induced itch. The same trend was observed for subjects who on average exhibited higher responses to the histamine-induced itch as for those who exhibited a much lower response.

EXAMPLE 3

Effect of topically applied Palmitoylethanolamide on histamine-induced itch.

In this demonstration, Palmitoylethanolamide (50 mM in ethanol) was mixed with Vaseline Intensive Care™ Lotion (abbreviated to VICL)(volume ratio 1:1). This mixture was applied (250 µl/5 cm$^2$–5 times at 1 h intervals) and histamine iontophoresis was performed on the treated site in the method described in Example 2. The vehicle control was ethanol:VICL (volume ratio 1:1). The procedure was carried out thrice, and the results summarised in Table 3 below.

TABLE 3

| | Treatment | Itch score (area under the curve) | Itch score % of control |
|---|---|---|---|
| Control | Vehicle alone | 3590 | 1000 |
| 3.1 | Vehicle + PEA | 1186 | 33 |
| Control | Vehicle alone | 622 | 100 |
| 3.2 | Vehicle + PEA | 103 | 16.5 |
| Control | Vehicle alone | 264 | 100 |
| 3.3 | Vehicle + PEA | 211 | 79.7 |

The results in Table 3 show that PEA can inhibit histamine-induced itch when topically applied to the skin in the presence of a lotion. This response occurs irrespective of whether the subjects were high or low itch responders.

EXAMPLE 4 (COMPARISON)

Effect of Topically Applied N-acyl Ethanolamides on Histamine-induced Itch.

Related molecules stearylethanolamine (SEA; 50 mM in ethanol) and linoleoylethanolamine (LAMEA; 50 mM in ethanol) were tested as potential activating agents for a CBR, employing the test method described in Example 3 and applied in the ethanol:VICL lotion. The results are summarised in Table 4 below

TABLE 4

| Treatment | | Itch score (area under the curve) | Itch score % of control |
|---|---|---|---|
| Control | Vehicle alone | 1770 | 100 |
| 4.1 | Vehicle + SEA | 3354 | 190 |
| 4.2 | Vehicle + LAMEA | 1768 | 100 |
| Control | Vehicle alone | 210 | 100 |
| 4.3 | Vehicle + LAMEA | 356 | 169 |
| 4.4 | Vehicle + SEA | 485 | 231 |
| Control | Vehicle alone | 1383 | 100 |
| 4.5 | Vehicle + SEA | 3593 | 260 |
| 4.6 | Vehicle + LAMEA | 1497 | 108 |

From Table 4, it can be seen by comparison with the relevant control that other N-acylethanolamines SEA and LAMEA were unable to demonstrate any anti-pruritic action or even appeared to exacerbate the itch response.

EXAMPLE 5

Skin Organotypic Culture Analysis of Palmitoylethanolamide

In this Example, skin organotypic cultures (Epiderm™, MatTek Inc, USA) were treated topically with an antiperspirant formulation (abbreviated to APF1) which is summarised in Table 5 below. Palmitoylethanolamide (PEA) was introduced into the medium. The cultures were then incubated at 37° C., 5% $CO_2$, and 95% relative humidity (standard cell culture conditions) for 24h. The culture medium was assayed for the pro-inflammatory cytokine interleukin-6 (IL-6). After water washing to remove the AP formulation, the viability of the culture was determined using the MTT assay. IL-6 was determined using an ELISA assay (R&D systems). The results are summarised in Table 6.

TABLE 5

| Trade Name | INCI Name | Supplier | % w/w |
|---|---|---|---|
| Rezal 67 | Al—Zr Pentachlorohydrate (40%) | Reheis | 50.00 |
| Distilled Water | Water | | 35.45 |
| DC245 | Cyclomethicone | Dow Corning | 4.00 |
| Emulgade SE | Glyceryl Stearate, Ceteareth-20, Ceteareth-12, Cetearyl Alcohol, Cetyl Palmitate | Cognis | 2.00 |
| Structure Solanace | Amphoteric Potato Starch | National Starch | 1.00 |
| | Parfum | | 1.00 |
| Polawax GP200 | Cetearyl Alcohol, PEG 20 Stearate | Croda | 0.65 |
| Cutina MD | Glyceryl Stearate | Cognis | 1.00 |
| Eumulgin B2 | Ceteareth-20 | Cognis | 0.40 |
| Eutanol G | Octyldodecanol | Cognis | 0.50 |
| Glycerol | Glycerine | Unichema | 4.00 |

TABLE 6

| Treatment | APF1 | PEA amount | IL-6 pg/ml ± SD |
|---|---|---|---|
| Base | no | no | 29.8 ± 3.5 |
| Control | yes | no | 86.3 ± 13.2 |
| 5.1 | yes | 0.1 $\mu$M | 38.3 ± 7.6 |
| 5.2 | yes | 1.0 $\mu$M | 36.5 ± 11.6 |
| 5.3 | yes | 10.0 $\mu$M | 59.5 ± 13.8 |
| 5.4 | yes | 100.0 $\mu$M | 43.0 ± 7.9 |
| 5.5 | yes | 1000.0 $\mu$M | 63.0 ± 24.8 |

From Table 6, it can be seen that PEA, at all concentrations used, was found to significantly decrease AP-induced IL-6 release from the cultures using Dunnet's test with a significance value of $p<0.05$. The reduction in the pro-inflammatory cytokine IL-6 indicates that the PEA will inhibit APF1-induced irritation. Culture viability of APF1 treatment alone was not significantly different from those of a combined APF1 and PEA treatment.

EXAMPLE 6

Effect of Palmitoylethanolamide on Antiperspirant-induced Irritation in vivo

In this Example, patch tests were performed on a mixed panel of 49 volunteers with age ranges between 18 and 55, using a double-blind protocol with randomized patch sites. Samples (20 mg) were applied to a filter paper that was placed within a Finn chamber (0.8 cm internal diameter). The chambers were then attached to the volar forearm using Scanpore™ tape (Norgesplater, Nor.) and left for 47 h. At the end of the 47 h period, the patches were removed and the site was left open for 5 h when the erythema associated with the patch was visually assessed and scored using an in-house standard assessment Patch Grading Scale as set out below. The results are summarised in Table 7 below.

TABLE 7

| Treatment | APF1 | PEA amount | Mean Irritation Score |
|---|---|---|---|
| Base | no | no | 0.28 |
| Control | yes | no | 0.67 |
| 6.1 | yes | 0.25% | 0.54 |

From Table 7, it can be seen that the APF1 formulation (a roll-on lotion) produced a significant increase in irritation score compared with no treatment—the base. Irritation was significantly mitigated by the incorporation of 0.25% palmitoylethanolamide into the base formulation. Statistical analysis was performed using a Wilcoxon signed rank test with a significance level of 5%. The conclusion from this analysis is that the irritation induced by patching the antiperspirant APF1 lotion was reduced significantly by the palmitoylethanolamide.

EXAMPLE 7

Effect of Topically Applied Anandamide (AEA) on Histamine-induced Itch

The demonstration method of Example 1 was followed except that AEA ((all Z)-N-(2-Hydroxyethyl)-5,8,11,14-eicosatetraenamide) was dissolved in Aqueous Cream BP at a concentration of 5% (w/v) instead of PEA. The results are summarised in Table 8 below.

TABLE 8

| Treatment | | Itch score (area under the curve) | Itch score % of control |
|---|---|---|---|
| Vehicle | AEA amount | | |
| Control yes | 0 | 1735 | 100 |
| 7.1 yes | 5% | 1322 | 76 |

From Table 8, it can be seen that the cannabinoid agonist anandamide is an inhibitor of histamine-induced itch when topically applied.

Methodology and Grading Scale

Histamine Iontophoresis Methodology

Histamine was applied iontophoretically to the skin using an Iontophoresis Controller MIC-e (Moor Instruments Ltd., Axminster) (Magerl, W., et al, J Invest.Dermatol., 94, 347–352 (1990)). The iontophoresis chamber was attached to the volar forearm using circular double adhesive rings. Histamine dihydrochloride (1%) dissolved in a methylcellulose gel (1%) in distilled water, was placed in the reservoir of the iontophoresis chamber and a platinum electrode in the chamber was connected to the positive terminal of the voltage source and a reference electrode (ECG electrode) fixed to the hand served as a cathode. One Laser Doppler probe (Channel 1) was inserted into the centre of the iontophoresis chamber to measure the changes in blood flow at the application site. A second Laser Doppler probe (Channel 2) was placed 1.5 cm distal to the stimulated area to assess the neurogenic mediated flare response. The probes were attached to DRT4 Dual Channel Laser Doppler Blood Flow Monitor that monitored continuously skin temperature and skin blood flow using solid-state lasers (MBF3D, Moor Instruments Ltd.). Measurements were taken for 60sec prior to insertion of the histamine solution into the chamber. This was followed by a 10sec period of 50 $\mu$A charge delivery, which applied 0.03 micromoles (0.57 $\mu$g) histamine into the skin. Blood flow was monitored continuously during an observation period of 5 min at a frequency of 40 Hz.

The subjects rated the itching sensation throughout the experiment by using a visual analogue scale (VAS), the output of which was monitored concurrently with blood flow changes. The subjects were instructed to assess the magnitude of the perceived pruritus (itch) on a linear analogue scale with the endpoints of 1 to 10, representing 'no itch' and 'unbearable itch' respectively. An intermediate reference point was set at 30% of the maximum, 4, representing the sensation of pruritus eliciting a desire to scratch the skin. VAS readings were taken for 5 min following histamine application and are expressed as area under the curve. Anti-itch agents were defined as materials which gave values of 80% or less compared with the vehicle alone.

Grading Scale for Patch and Cream Cover

TABLE 9

| Description | Grade |
|---|---|
| 0.0 | No apparent cutaneous involvement. |
| 0.5 | Faint, barely perceptible erythema or slight dryness |
| 1.0 | Faint but definite erythema, no eruptions or broken skin or no erythema but definite dryness; may have epidermal fissuring. |
| 1.5 | Well defined erythema or faint papules with definite dryness, may have epidermal fissuring. |
| 2.0 | Moderate erythema, may have very few papules or deep fissures, moderate to severe erythema in the cracks. |
| 2.5 | Moderate erythema with barely perceptible oedema or severe erythema not involving a significant portion of the patch (halo effect around the edges), may have a few papules or moderate to severe erythema. |
| 3.0 | Severe erythema (beet redness), may have generalized papules or moderate to severe erythema with slight oedema (edges well defined by raising). |
| 3.5 | Moderate to severe erythema with moderate oedema (confined to patch area) or moderate to severe erythema with isolated eschar formations or vesicles. |
| 4.0 | Generalized vesicles or eschar formations or moderate to severe erythema and/or oedema extending beyond the area of the patch. |

Further Examples of Formulations According to the Present Invention are Described Hereinafter In the subsequent Tables herein, the following abbreviations are employed AACH Activated aluminium chlorohydrate ACH Aluminium chlorohydrate AZH Aluminium Zirconium chlorohydrate AZAG Aluminium Zirconium Chlorohydrate Glycine complex PHMB Polyhexamethylene biguanide—Cl or Stearate salt EDTA Ethylene diamine tetraacetic acid DEA Diethanolamide POE polyoxyethylene Lotion Formulations

TABLE 10

| Example No | 8.1 | 8.2 | 8.3 |
|---|---|---|---|
| Constituent | Percent by weight | | |
| Example No | 4 | 5 | 6 |
| Ethanol | | 30 | |
| Isopropanol | 30 | | |
| Hydroxypropyl-cellulose | 0.7 | 0.7 | |
| ACH | 20 | | |
| AZH | | 20 | |
| AZAG | | | 20 |
| PHMB | | | |
| Triclosan | | | |
| Palmitoy-lethanolamide | 1.0 | 1.2 | 1.5 |
| Suspending Agent | | | 3 |
| Propylene Carbonate | | | 1 |
| Glycerol | 2 | 2 | |
| Talc | | | 6 |
| Water + minors | to 100 | to 100 | |
| Cyclomethicone DC245 + minors | | | to 100 |

Lotion formulations can be applied using a roll-on, or with the exception, in some countries, of zirconium salt-containing formulations, by a pump spray.

Stick Formulations

TABLE 11

| Constituent | 9.1 | 9.2 | 9.3 | 9.4 | 9.5 | 9.6 |
|---|---|---|---|---|---|---|
| | | | Example No % by weight | | | |
| Cyclomethicone (DC245) | 39.8 | 36.8 | 35.8 | 39.9 | 39.75 | 46.5 |
| Permethyl 103A | 16 | 12 | | | | |
| Mineral Oil | | | 11.5 | | | |
| PPG-14 Butyl ether | | 4 | | 10 | | |
| Dimethicone (50 cs) | | | 1.5 | | | |
| Stearyl alcohol | 14 | 14 | 14 | 17 | 11.5 | |
| Castor wax | 2 | 5 | 4.5 | 2.5 | 5 | |
| 12-hydroxystearic acid | | | | | | 6 |
| N-lauroyl glutamic acid Dibutylamide | | | | | | 2 |
| Eicosanol | 0.2 | 0.2 | 0.2 | | | |
| Octyldodecanol | | | | 14 | 14 | |
| C20–40 alcohols | | | | | | 0.5 |
| C$_{20-40}$ pareth-3/C$_{20-40}$ pareth-20 | | | | | 1.75 | |
| PEG-8 distearate | | | | 0.6 | | 5 |
| Al—Zr Gly antiperspirant active | 23 | 25 | | 24 | 26 | 26 |
| Aluminium chlorohydrate | | | 26 | | | |
| Glycerol | | | 2 | 2 | | |
| EDTA | | | | | 1 | |
| Talc | 3 | | 1.5 | | | |
| Fumed Silica | | 1 | 1 | 2 | | |
| palmitoyl ethanolamide | 1 | 1 | 1 | 1 | 1 | 1 |
| Fragrance | 1 | 1 | 1 | 1 | | |

| Constituent | 9.7 | 9.8 | 9.9 | 9.10 |
|---|---|---|---|---|
| | | Example No. % by weight | | |
| Cyclomethicone (DC245) | 48 | 10 | 37 | |
| Polydecene | | 12.7 | | |
| PPG-14 Butyl ether | | 2.5 | | |
| C12–15 alkyl benzoate | | | 15 | |
| propylene glycol | | | | 48.3 |
| ethanol | | | | 13 |
| isostearyl alcohol | | | | 12 |
| dextrin palmitate | 10 | | | |
| cellobiose octanonanoate | | 3.8 | | |
| beta sitosterol | | | 2.5 | |
| oryzanol | | | 2.5 | |
| dibenzylilidene sorbitol | | | | 3 |
| Isopropyl myristate | 10 | | | |
| Cetyl dimethicone copolyol | | 1 | 1 | |
| Amino-2-methyl-1-propanol | | | | 0.2 |
| Al—Zr Gly antiperspirant active | | | | 22.5 |
| Aluminium chlorohydrate | 30 | | | |
| Zirkonal 50 | | 51.7 | 40 | |
| Glycerol | | 17.3 | | |
| palmitoyl ethanolamide | 1 | 1 | 1 | 1 |
| Fragrance | 1 | | 1 | |

Cream or Soft Solid Formulations

TABLE 12

| Ingredients | 10.1 | 10.2 | 10.3 | 10.4 | 10.5 | 10.6 | 10.7 |
|---|---|---|---|---|---|---|---|
| | | | Example No % by weight | | | | |
| Silicone wax | | 2.5 | | | 3 | | |
| Syncrowax ERLC (13) | | 2.5 | 5 | | | | |
| Synchrowax HGL-C | | | 1.25 | | | | |
| Castor wax | | 7.5 | | | | | |
| Triacontenyl vinyl pyrrolidone copolymer | 5 | | | | | | |
| Paraffin wax | 5 | 7.5 | | | | | |
| Silica | | | 1 | | | 1.5 | 1.5 |
| Talc | | | | 1.75 | | | 6 |
| Hydrohobic Clay Bentone 38 | | | | | | | 3 |
| Anhydrous aluminium silicate | | | | | | | 6 |
| Microthene powder | | | | | | | 6 |
| Propylene Carbonate | | | | | | | 1.5 |
| Cyclomethicone | | 63.5 | | | 60.5 | 62.5 | 38.3 |
| Tetraphenyl tetramethylsiloxane | | | | 52 | | | |
| C12–15 Alkyl benzoate | 63.5 | | 62.5 | | | 10 | |
| Dextrin palmitate | | | | 5 | | | |
| Octyldodecanol | | | | 15 | | | |
| Dimethicone 10 cst | | | | | 5 | | 10 |
| POE 100 stearyl ether | | | | | | | 2 |
| AACH | 25 | 25.5 | | | | 22 | |
| Milled AACH | | | 25.5 | 25.5 | | | |
| AZAG 7167 | | | | | 25 | | 26.7 |
| Palmitoyl ethanolamide | 1 | 1 | 1 | 1 | 1 | 1 | 1 |
| Fragrance | 0.5 | | | | 0.5 | | |

| Ingredients | 10.8 | 10.9 | 10.10 | 10.11 | 10.12 | 10.13 |
|---|---|---|---|---|---|---|
| | | | % by weight | | | |
| Cetearyl dimethicone/vinyl dimethicone crosspolymer and Cyclopentasiloxane | | | | | | 62.1 |
| Syncrowax ERLC (13) | | | | | 3.75 | |
| Castor wax | 4 | | | | 1.25 | |
| Stearyl alcohol | 6 | | | | | |
| Candelilla wax | | 7 | | | | |
| C24/28 alkyl dimethicone wax | | 3.5 | | | | |
| Silica | | | | | | 0.2 |
| Talc | 5 | | | | | |
| Hydrohobic Clay Bentone 38 | | 0.5 | | | | |
| Cyclomethicone | 58 | 45 | 49.8 | — | | |
| C12–15 Alkyl benzoate | | | 12.7 | 62.5 | 63.5 | 4 |
| Dextrin palmitate | | | 10 | 10 | 5 | |
| Neopentyl Glycol Diheptanoate | | | | | | 5 |
| PPG14 Butyl ether | 4.5 | | | | | |
| Dimethicone 350 cst | | 25 | | | | |
| PEG8 distearate | | | | | | 2 |
| Stearyl dimethicone | | | | | | 0.75 |
| POE 100 stearate | 1 | | | | | |
| PPG1-PEG9-lauryl glycol ether | | | | | | 2 |
| AACH | | | — | | 25.5 | |
| Milled AACH | | | | 26 | | |
| ACH | | 18 | — | | | |
| AZAG 7167 | 20 | | 26.5 | | | 22.45 |
| Palmitoyl ethanolamide | 1 | 1 | 1 | 1 | 1 | 1 |
| Fragrance | 0.5 | | | 0.5 | | 0.5 |

Aerosol Formulations

TABLE 13

| Constituents | 11.1 | 11.2 | 11.3 | 11.4 | 11.5 | 11.6 |
|---|---|---|---|---|---|---|
| | | | % by weight | | | |
| Cyclomethicone DC245 | 3.5 | 11.95 | 14.8 | 3.8 | 4.6 | 5.6 |
| Ethanol | | 20 | | | | |
| Isopropylpalmitate | | | 10.5 | | 9.4 | |
| Isopropyl myristate | | | | | | 0.31 |
| PPG-14 Butyl ether | 9.7 | 0.7 | | | | 9.7 |
| Octyldodecanol | | 0.25 | | | | |
| Polydecene | | | | | | 0.3 |
| Dibutyl phthalate | | | | 4.5 | | |
| Quaternised Clay - Bentone 38 | 1 | 1 | 1.5 | 1 | 0.95 | 0.7 |
| Propylene carbonate | | | | | 0.15 | |
| Methylpropanolamine | | | | | | 0.08 |
| Silicone gum (Q2- | | | | 0.2 | | |

TABLE 13-continued

| Constituents | 11.1 | 11.2 | 11.3 | 11.4 | 11.5 | 11.6 |
|---|---|---|---|---|---|---|
| | % by weight | | | | | |
| 1401) | | | | | | |
| AACH | | 10 | | 4 | | |
| Milled AACH | 10 | | | | | 2 |
| ACH | | | 9.2 | | 9.3 | |
| Silica | | 0.1 | | | | 0.01 |
| Talc | | | 3 | | | |
| Micronised polyethylene | | | | | 9.3 | |
| Perfume | 0.5 | 0.7 | 0.7 | 0.7 | | 1 |
| Allantoin | | | | | 1.5 | |
| Palmitoyl ethanolamide | 0.3 | 0.3 | 0.3 | 0.3 | 0.3 | 0.3 |
| n-Pentane | | | | 20 | | |
| C3/C4 hydrocarbon mixture | 75 | 75 | 40 | 70 | 60 | 80 |

The cyclomethicone DC245 in the formulations in Tables 10, 11, 12 or 13 hereinabove can be replaced wholly or partly by DC345.

We claim:

1. An antiperspirant or deodorant cosmetic composition suitable for topical application to the human skin, comprising:
   i. an antiperspirant or deodorant active comprising an aluminium and/or zirconium salt or complex;
   ii. a carrier for the antiperspirant or deodorant active; and
   iii. an effective amount of a CBR activating agent.

2. A composition according to claim 1 in which the amount of the CBR activating agent is selected in the range of from 0.05 to 20% by weight and preferably 0.5 to 10% by weight.

3. A composition according to claim 2 in which the amount of the CBR activating agent is selected in the range of from 0.5 to 10% by weight.

4. A composition according to claim 1 in which the CBR activating agent is selected from:
   2-arachidonyl-glycerol
   1-arachidonyl-glycerol
   3-arachidonyl-glycerol
   2-linoleoyl-glycerol
   2-linolenoyl-glycerol
   2-eicosatrienoyl-glycerol
   2-eicosatetraenoyl-glycerol
   2-eicosapentenoyl-glycerol
   2-eicosahexaenoyl-glycerol
   palmitoylethanolamide
   (6aR)-trans-3-(1,1-Dimethylheptyl)-6a,7,10,10a-tetrahydro-1-hydroxy-6,6-dimethyl-6H-dibenzo[b,d]pyran-9-methanol, sometimes called HU-210 herein;
   Indomethacin morpholinylamide;
   mesylate: (R)-(+)-[2,3-Dihydro-5-methyl-3-(4-morpholinylmethyl)pyrrolo[1,2,3-de]-1,4-benzoxazin-6-yl]-1-naphthalenylmethanone; and
   (−)-cis-3-[2-Hydroxy-4-(1,1-dimethylheptyl)phenyl]-trans-4-(3-hydroxypropyl) cyclohexanol.

5. A composition according to claim 4 in which the CBR activating agent is palmitoylethanolamide.

6. A composition according to claim 1 in which the antiperspirant active (i) comprises from 10 to 30% by weight of the composition.

7. A composition according to claim 1 in which the antiperspirant active contains zirconium.

8. A composition according to claim 1 in which the antiperspirant active (i) and the CBR activating agent (iii) are present in a weight ratio of from 5:1 to 50:1.

9. A composition according to claim 1 in which the carrier (ii) comprises a volatile silicone carrier.

10. A composition according to claim 8 in which the volatile silicone carrier is present in an amount of from 10 to 70 wt %.

11. A composition according to claim 1 in which the carrier (ii) comprises a structurant or thickening agent in a concentration sufficient to produce a stick or cream.

12. A composition according to claim 1 which comprises base composition which forms an aerosol composition together with a propellant, the weight ratio of propellant to base composition being selected within the range of from 40:60 to 99:1.

13. A method of reducing or eliminating irritancy arising from topical application of an antiperspirant or deodorant cosmetic composition comprising an antiperspirant or deodorant active comprising an aluminium and/or zirconium salt or complex and a carrier characterised by incorporating in the composition an effective amount of a CBR activating agent.

14. A method of reducing or eliminating sweat or body odour and ameliorating or eliminating concomitant irritancy by applying topically to human skin a composition containing an antiperspirant and/or deodorant active material comprising an aluminium and/or zirconium salt or complex which further contains an effective amount of a CBR activating agent.

* * * * *